United States Patent
Wessjohann et al.

(10) Patent No.: US 7,381,743 B2
(45) Date of Patent: Jun. 3, 2008

(54) MACROCYCLES FOR THE TREATMENT OF CANCER

(75) Inventors: Ludger A. Wessjohann, Halle (DE); Uwe Eichelberger, Priester (DE); Thao Tran Thi Phuong, Dong Da Ha Noi (VN)

(73) Assignee: Leibniz-Institut Fuer Pflanzenbiochemie (IPB), Halle (DE)

( * ) Notice: Subject to any disclaimer, the term of this patent is extended or adjusted under 35 U.S.C. 154(b) by 0 days.

(21) Appl. No.: 10/580,992

(22) PCT Filed: Nov. 26, 2004

(86) PCT No.: PCT/EP2004/013451

§ 371 (c)(1),
(2), (4) Date: Dec. 21, 2006

(87) PCT Pub. No.: WO2005/051947

PCT Pub. Date: Jun. 9, 2005

(65) Prior Publication Data

US 2007/0105905 A1  May 10, 2007

(30) Foreign Application Priority Data

Nov. 26, 2003 (DE) .................. 103 55 223

(51) Int. Cl.
- *A01N 43/02* (2006.01)
- *A01N 43/22* (2006.01)
- *A61K 31/38* (2006.01)
- *C07D 267/22* (2006.01)
- *C07D 281/18* (2006.01)

(52) U.S. Cl. ............... 514/431; 514/450; 514/456; 540/455; 540/454

(58) Field of Classification Search .......... 540/455, 540/454; 514/431, 450, 456
See application file for complete search history.

(56) References Cited

FOREIGN PATENT DOCUMENTS

| DE | 41 38 042 A1 | 5/1993 |
|---|---|---|
| DE | 198 20 599 A1 | 11/1999 |
| WO | WO 03/078411 A | 9/2003 |

OTHER PUBLICATIONS

Freshney (Culture of Animal Cells, A Manual of Basic Technique, Alan R. Liss, Inc., 1983, New York, p. 4).*
Dermer (Bio/Technology, 1994, 12:320).*
Terasawa et al., "Reaction of Mixed Carboxylic Anhydrides with Grignard Reagents," *Tetrahedron*, vol. 33, 595-598 (1997), XP002318906.

* cited by examiner

*Primary Examiner*—Margaret D. Seaman
*Assistant Examiner*—Niloofar Rahmani
(74) *Attorney, Agent, or Firm*—Leydig, Voit & Mayer, Ltd.

(57) ABSTRACT

The present invention relates to new macrocycles of the general formula (I) as well as their use for the treatment of cancer diseases

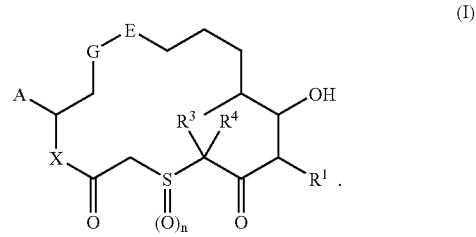

11 Claims, No Drawings

MACROCYCLES FOR THE TREATMENT OF CANCER

This application is the U.S. national phase of International Patent Application PCT/EP2004/013451, filed on Nov. 26, 2004, which claims priority to German Patent Application No. 103 55 223.5, filed Nov. 260, 2003, all of which are hereby incorporated by reference.

Epothilones (DE 4138042) are natural products with exceptional biological effects, for example as mitosis inhibitors, microtubuli-modifying agents, cytotoxics or fungicides. In particular they show paclitaxel-similar properties and still surpass Paclitaxel (Taxol™) in some tests in activity. There are currently some derivates in clinical studies for the treatment of several cancers (Nicolaou et al. Angew. Chem. Int. Ed. 1998, 37, 2014-2045; Flörsheimer et al. Expert Opin. Ther. Patents 2001, 11, 951-968).

It was objective of the present invention to provide new epothilone-like derivates which show a better profile concerning their preclinical and clinical development potential.

The present invention provides compounds of the general formula (I):

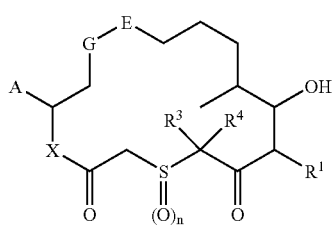

wherein

A is a heteroalkyl-, a heterocycloalkyl-, a heteroalkyl cycloalkyl-, a heteroaryl- or a heteroarylalkyl group, preferentially a heteroarylalkyl or a heteroaryl group, G-E is selected from the following groups,

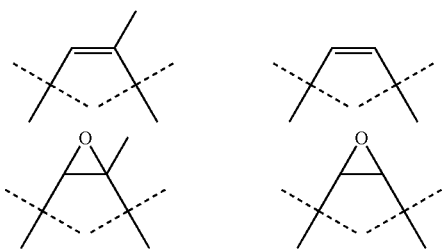

or is part of an optionally substituted cyclopropyl ring, in all of the groups the preferred methyl group (methyl branching) can be substituted by another alkyl group, most preferred for G-E ist the —(CH)=C(Me)- group, especially in Z-configuration, n is 0, 1, or 2, $R^1$ is a hydrogen, $C_1$-$C_4$ alkyl- or a $C_3$-$C_4$-Cycloalkyl group, preferentially a methyl or ethyl group, X is oxygen or a group of the formula $NR^2$, wherein $R^2$ is hydrogen, OH, $NH_2$, NH(alkyl), N(alkyl)$_2$, an alkyl-, alkenyl-, alkynyl-, heteroalkyl-, aryl-, heteroaryl-, cycloalkyl-, alkylcycloalkyl-, heteroalkylcycloalkyl-, heterocycloalkyl-, aralkyl- or a heteroaralkylrest, $R^3$ and $R^4$ are independent of each other a hydrogen atom, a $C_1$-$C_4$-alkyl group or together part of a cycloalkyl group with 3 or 4 ring atoms, preferably $C_1$-$C_4$-alkyl, specially preferred both are methyl groups, or a pharmacologically acceptable salt, solvate, hydrate or a pharmacologically acceptable formulation of the same ones.

The term alkyl refers to a saturated, straight or branched chain alkyl group, containing from 1 to 20 carbon atoms, preferably from 1 to 12 carbon atoms, more preferably containing 1 to 6 carbon atoms, for example the methyl-, ethyl-, isopropyl-, isobutyl-, tert-butyl, n-hexyl-, 2,2-dimethylbutyl- or n-octyl group.

The terms alkenyl and alkynyl refer at least in part to unsaturated, straight or branched chain alkyl groups that containing from 2 to 20 carbon atoms, preferably from 2 to 12 carbon atoms, more preferably containing from 2 to 6 carbon atoms, for example the allyl-, acetylenyl-, propargyl-, isoprenyl- or hex-2-enyl-group.

The term heteroalkyl refers to a alkyl-, a alkenyl- or a alkynyl group, wherein one or more (preferably 1, 2 or 3) carbon atoms are replaced by an oxygen-, nitrogen-, phosphorus, boron or sulphur atom (preferably oxygen, sulphur or nitrogen), for example an alkyloxy group, as for example methoxy or ethoxy, or a methoxymethyl-, nitrile-, methylcarboxyalkylester- or 2,3-dioxyethyl-group. The term heteroalkyl refers furthermore to a carboxylic acid or a group derived from a carboxylic acid as for example acyl, acyloxy, carboxyalkyl, carboxyalkylester, such as for example methylcarboxy-alkylester, carboxyalkylamide, alkoxycarbonyl or alkoxycarbonyloxy.

The term cycloalkyl or, respectively cyclo- refers to a satisfied or partially unsaturated cyclic group, having one or more rings, formed by 3 to 14 carbon atoms, preferably 3 to 10 carbon atoms, for example the cyclopropyl-, cyclohexyl-, tetralin- or cyclohex-2-enyl-group.

The term heterocycloalkyl or, respectively heterocyclo-, refers to a cycloalkyl group as defined above, wherein one or more (preferably 1, 2 or 3) carbon atoms are replaced by an oxygen-, nitrogen, phosphorus or sulphur atom, such as for example the piperidine-, morpholine-, tetrahydrofuran-, tetrahydrothiophen-, N-methylpiperazine or N-phenylpiperazine group.

The terms alkylcycloalkyl or, respectively heteroalkylcycloalkyl, refer to groups, that according to the above definitions contain both cycloalkyl- or, respectively heterocyclo-alkyl, as well as alkyl-, alkenyl-, alkynyl- and/or heteroalkyl groups.

The term aryl or, respectively Ar refers to an aromatic group that has one or more rings, formed by 5 to 14 carbon atoms, preferably 5 or 6 to 10 carbon atoms, for example a phenyl-, naphthyl-, 2-, 3- or 4-methoxyphenyl-, 2-, 3- or 4-ethoxyphenyl-, 4-carboxyphenylalkyl- or 4-hydroxyphenyl group.

The term heteroaryl refers to an aryl group, wherein one or more (preferably 1, 2 or 3) carbon atoms are replaced by an oxygen-, nitrogen, phosphorus or sulphur atom, such as for example 4-pyridyl-, 2-imidazolyl-, 3-pyrazolyl-, oxazolyl-, thiazolyl-, thiophene and isochinolinyl group.

The terms aralkyl or, respectively heteroaralkyl refer to groups, that according to the above definitions comprise of both aryl- or, respectively heteroaryl- as well as alkyl-, alkenyl-, alkynyl- and/or heteroalkyl- and/or cycloalkyl- and/or heterocycloalkyl groups, for example the tetrahydroisochinolinyl-, benzyl, 2- or 3-ethyl-indolyl- or 4-methylpyridino group.

The terms alkyl, alkenyl, alkinyl, heteroalkyl, cycloalkyl, heterocycloalkyl, aryl, heteroaryl, aralkyl and heteroaralkyl as well as "optionally substituted" refer also to groups, in which one or more hydrogen atoms of such groups are replaced through fluorine, chlorine, bromine or iodine atoms or through OH, SH, $NH_2$ or $NO_2$ groups. These terms refer additionally to groups, which are substituted with unsubstituted alkyl-, alkenyl-, alkynyl-, heteroalkyl-, cycloalkyl-, heterocycloalkyl-, aryl-, heteroaryl-, aralkyl- or heteroaralkyl groups as defined herein.

Compounds of the formula (I) can contain one or more chirality centers due to their substitution pattern. The present invention comprises of therefore both all pure enantiomers and all pure diastereoisomers, as well as also their mixtures in every possible ratio of the mixtures. Furthermore, the present invention also comprises of all cis/trans-isomers of the compounds of the general formula (I) as well as their mixtures.

Preferred are compounds of the formula (I), wherein A is a group of the formula is $-C(CH_3)=CHR^5$ or $-CH=CHR^5$, wherein $R^5$ is a heteroaryl- or a heteroarylalkyl group.

Further prefered are compounds of the formula (I), wherein A is a group of the general formula (II) to (V), preferentially (II) or (III):

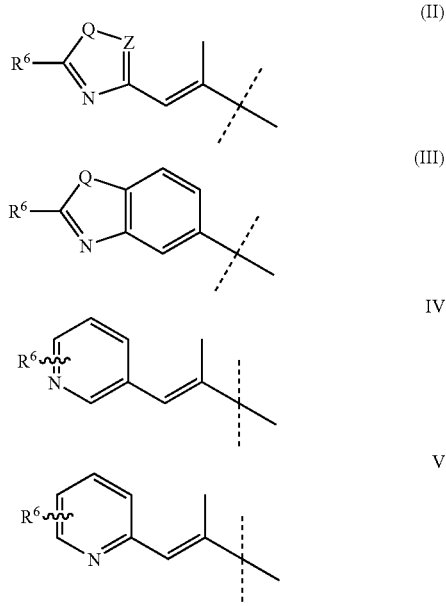

wherein Q sulphur, oxygen or a group of the formula $NR^7$ wherein $R^7$ is hydrogen, a $C_1$-$C_4$ alkyl group or a $C_1$-$C_4$-heteroalkyl group, z is nitrogen or a CH group and $R^6$ is a group of the formula $OR^8$ or $NHR^8$, a alkyl-, alkenyl, alkynyl- or a heteroalkyl group (preferably a group of the formula $CH_2OR^8$ or $CH_2NHR^8$), wherein $R^8$ is a hydrogen, a $C_1$-$C_4$ alkyl group or a $C_1$-$C_4$-heteroalkyl group (preferably a hydrogen atom).

Z is especially preferred a CH group.

Moreover preferred are compounds of the formula (I) wherein Q is sulphur or oxygen.

Further preferred are compounds of the formula (I), wherein $R^6$ is a group of the formula $CH_3$, $CH_2OH$ or $CH_2NH_2$.

Further preferred $R^2$ is a hydrogen atom or a $C_1$-$C_4$ alkyl group (especially preferred a hydrogen atom).

Furthermore preferred are compounds of the formula (I), wherein X is oxygen.

Additionally preferred $R^1$ is a methyl, ethyl- or propyl group; especially preferred a methyl group.

Further preferred $R^3$ and $R^4$ are methyl groups.

Examples of pharmacologically acceptable salts of compounds of the formula (I) are salts (or mixed salt) of physiologically acceptable mineral acids such as hydrochloric acid, sulphuric acid and phosphoric acid or salts of organic acids such as methanesulphonic acid, p-toluenesulfonic acid, lactic acid, acetic acid, trifluoroacetic acid, citric acid, succinic acid, fumaric acid, maleic acid and salicylic acid. Compounds of the formula (I) may be solvated, especially hydrated. The hydratisation can occur for example during the process of production or as a consequence of the hygroscopic nature of the initially anhydrous compounds of the formula (I). If the compounds of the Formula (I) contain asymmetric C-atoms, they may be present either as achiral compounds, diastereoisomer-mixtures, mixtures of enantiomers or as optically pure compounds. Furthermore, the present invention relates also to all cis/trans-isomers of the present compounds of the general Formula (I) as well as their mixtures.

The pharmaceutical compositions according to the present invention contain at least a compound of the formula (I) as active agent and optionally carriers and/or adjuvants.

The present invention also relates to pro-drugs (for a definition and examples see R. B. Silverman, Medical Chemistry, VCH Weinheim, 1995, chapter 8, p. 361ff), which are composed of a compound of the Formula (I) and at least one pharmacologically acceptable protective group which will be cleaved off under physiological conditions, for example a alkoxy, aralkyloxy, acyl or acyloxy group, such as ethoxy-, benzyloxy-, acetyl or acetyloxy group.

Except for the already described cancer diseases the compounds of the present invention are of great interest for the treatment of further diseases such as autoimmune diseases, inflammatory diseases, tumor diseases and other diseases which are to be connected to failure or disturbance of cell growths.

The present invention also relates to the therapeutic use of the compounds of the Formula (I), their pharmacologically acceptable salts and/or solvates and hydrates as well as their formulations and pharmaceutical compositions.

Also the use of these active agents for the production of drugs for the treatment of cancer diseases is object of the present invention. In general, compounds of the Formula (I) will be administered by using the known and acceptable modes known in the art, either separately or in combination with any other therapeutic agent. Such therapeutically useful agents can be administered by one of the following routes: oral, e.g. as dragees, coated tablets, pills, semisolids, soft or hard capsules, solutions, emulsions or suspensions; parenteral, for example as injectable solution; rectal as suppositories; by inhalation, for example as powder formulation or spray, transdermal or intranasal. For the production of such tablets, pills, semisolids, coated tablets, dragees and hard gelatin capsules the therapeutically useful product may be mixed with pharmaceutically inert, inorganic or organic excipients, as are for example lactose, sucrose, glucose, gelatin, malt, silica gel, starch or derivates thereof, talc, stearic acid or their salts, dry skim milk and the like. For the production of soft capsules one may use excipients as are for example vegetable oils, petroleum or paraffin, animal or synthetic oils, wax, fat, polyols. For the production of liquid solutions and syrups one may use excipients as for example water, alcohols, aqueous saline, aqueous dextrose, polyols, glycerin, vegetable oils, petroleum, animal or synthetic oils. For suppositories one may use excipients as for example vegetable oils, petroleum or paraffin, animal or synthetic oils, wax, fat and polyols. For aerosol formulations one may use compressed gases suitable for this purpose as for example oxygen, nitrogen, rare gases and carbon dioxide. The pharmaceutically useful agents may also contained additives for conservation, stabilization, emulsifiers, sweeteners, flavors, salts for the change of the osmotic pressure, buffers, coating additives and antioxidants.

Combinations with other therapeutic agents may include other therapeutically useful agents which usually are used for the treatment of cancer diseases.

For the treatment of cancer diseases the dose of the biologically active compound related to this invention can vary within wide borders|boundaries and can be adjusted to the individual needs. In general, a dose of 1 µg to 100 mg/kg body weight per day is appropriate, with a preferred dose of 10 µg to 25 mg/kg per day. In appropriate cases the dose may be also lower or higher than the values given above.

EXAMPLES

The synthesis of the "northern half alcohol" is described in WO 0232844.

Southern Half Building Block A (NOT to be Mistaken for Substituent A in I)

A1)

2-bromo-2-methyl-pentan-3-one

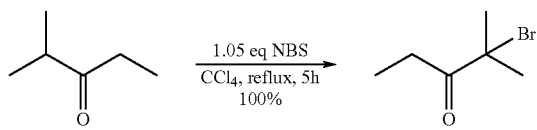

N-Bromosuccinimide (1.86 g, 10.5 mmol) was added to a solution of 2-methyl-3-pentanone (1 g, 10 mmol) in carbon tetrachloride (10 ml). The mixture was boiled under efficient illumination for 4 h. After cooling, the mixture was filtered at the pump, the filtrate washed successively with water (5 ml), aqueous sodium bicarbonate solution (5 ml), and finally with water (5 ml). After drying (Na$_2$SO$_4$), the excess of solvent was removed by evaporation under reduced pressure. Purification on silica column petroleum ether (PE): ethyl acetate (EA) 25:1. Yield : 1.79 g (100%). $^1$H-NMR (400 MHz, CDCl$_3$): δ=1.13 (t, J=7.4 Hz, 3H), 1.87 (s, 6H), 2.85 (q, J=7.4 Hz, 2H).

A2) ethyl[(1,1-dimethyl-2-oxobutyl)thio]acetate

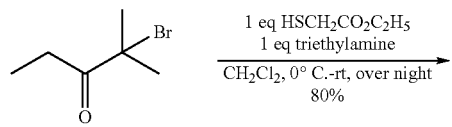

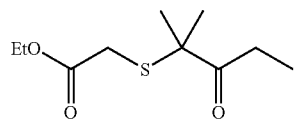

To a solution of 2-bromo-2-methyl-pentan-3-one (A1) (13.5 g, 75 mmol) in CH$_2$Cl$_2$ (400 ml) were added ethyl 2-mercaptoacetate (9 g, 8.2 ml, 75 mmol) and 10.42 ml triethylamine at 0° C. and stirred for 3 h. The solution was allowed to come to room temperature (12 h). The resulting suspension was filtered, the filtrate washed with water (100 ml) and brine (100 ml) and dried over Na$_2$SO$_4$. Removal of the solvent in vacuo gave a slightly yellow oil, which was purified by flash chromatography (ethyl acetate-petroleum ether 1:25).

$^1$H-NMR (400 MHz, CDCl$_3$): δ=1.06 (t, 3H, J=7.0 Hz), 1.15 (t, 3H, J=7.0 Hz), 1.44 (s, 6H), 2.74 (q, 2H, J=7.4 Hz), 3.15 (s, 2H), 4.15 (q, 2H, J=7.4 Hz) ppm.

A3)

[(1,1-dimethyl-2-oxobutyl)thio]acetic acid

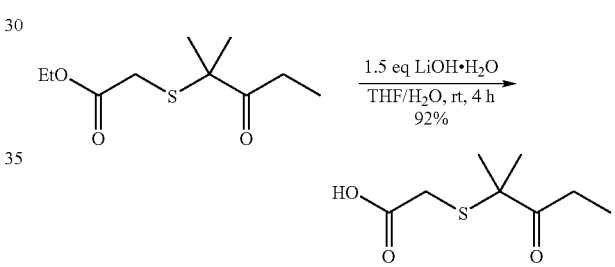

To a solution of ethyl[1,1-dimethyl-2-oxobutyl)thio]acetate (A2) (18 g, 82 mmol) in THF/water (3:1, 400 ml), solid LiOH*H$_2$O (6.88 g, 164 mmol) was added. The mixture was stirred for 4 h at room temperature, diluted with water and then acidified to pH 2 by treatment with 6M hydrochloric acid. The aqueous layer was extracted with diethyl ether (2×100 ml) and the combined organic layers were washed with water (100 ml) and dried over Na$_2$SO$_4$. Evaporation of the solvents gave the crude product, which was purified by column chromatography (PE:EA 1:1+1% acetic acid).

$^1$H-NMR (400 MHz, CDCl$_3$): δ=1.05 (t, J=7.0 Hz, 3H), 1.25 (s, 1H), 1.47 (s, 6H), 2.73 (q, J=7.0 Hz, 2H), 3.21 (s, 2H)

A4)

(2-Methyl-3-oxo-pentan-2-sufinyl)-essigsäure

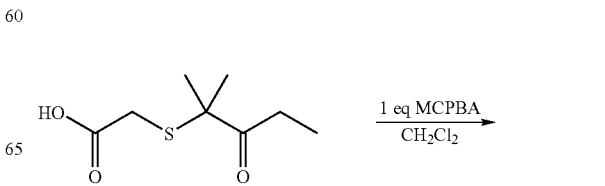

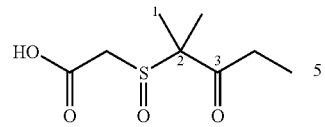

To (1,1-Dimethyl-2-oxo-butylsulfanyl)-acetic acid (A3) (0.25 g, 1.32 mmol) in CH$_2$Cl$_2$ (5 ml) is added metachlorperbenzoic acid (0.23 g, 1.32 mmol) and kept at 0° C. for 3 h. Water (5 ml) and acetic acid are added, and the mixture is extrtacted with ethyl acetate (3×10 ml). The organic phase is dried over Na$_2$SO$_4$, the solvent removed in vacuo and the residue chromatograped (PE:EA 1:1+1% acetic acid).

$^1$H-NMR (300 MHz, CDCl$_3$): δ=0.98-1.05 (m, 3H, CH$_3$-5), 1.43, 1.48 (2×s, 6H, CH$_3$-1, 2-CH$_3$), 2.53-2.79 (m, 2H, CH$_2$-4), 3.37, 3.54 (2×d, 2H, SCH$_2$), 8.82 (bs, 1H, OH) C$_8$H$_{14}$O$_4$S (206.26, 206.06), HRMS: calcd (M+Na)$^+$ 229.0505, found 229.0510

A5)

[(3-bromo-1,1-dimethyl-2-oxobutyl)thio]acetic acid

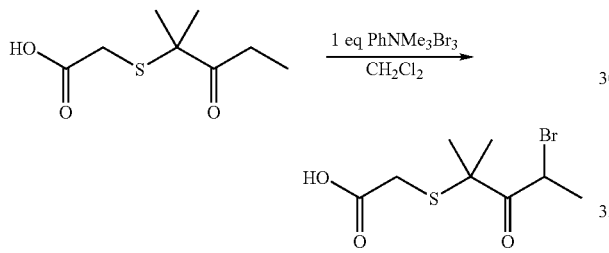

To a solution of [(1,1-dimethyl-2-oxobutyl)thio]acetic acid (0.3 g, 1.58 mmol) in CH$_2$Cl$_2$ (10 ml) was added phenyltrimethylammonium tribromide (0.62 g, 1.65 mmol) at 0° C. After stirring for 15 min, the solution was allowed to come to room temperature and stirring was continued for 1 h. Water (30 ml) was added and the aqueous layer was extracted with diethyl ether (15 ml). The combined organic layers were washed with brine (25 ml), dried over Na$_2$SO$_4$, filtered and concentrated in vacuo. The remaining oil was purified by flash chromatography (ethyl acetate-petroleum ether 1:1 containing 0.1% glacial acetic acid). Yield: 0.39 mg (91%). $^1$H-NMR (400 MHz, CDCl$_3$): δ=1.15, 1.64 (2×s, 6H, C(CH$_3$)$_2$), 1.81 (d, 3H, J=7.0 Hz), 3.14, 3.21 (2×d, 2H, J=6.8 Hz), 5.07 (q, 1H, J=7.0 Hz) ppm. C$_8$H$_{13}$BrO$_3$S (269.16, 267.98), HRMS: calcd (M+Na)$^+$ 290.9661, found 290.9669.

A6)

[(3-bromo-1,1-dimethyl-2-oxobutyl)sulfonyl]acetic acid

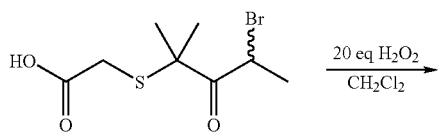

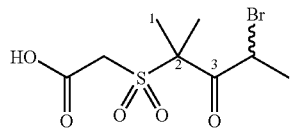

To a solution of [(3-bromo-1,1-dimethyl-2-oxobutyl)thio] acetic acid (0.77 g, 2.9 mmol) in acetic acid (6 ml), H$_2$O$_2$ (30%, 1.91 g, 56 mmol) was added and the mixture was stirred for 4 h. It was extracted with ethyl acetate (3×10 ml), dried over Na$_2$SO$_4$ and the solvents were evaporated under reduced pressure. The remaining oil was purified by flash chromatography (ethyl acetate-petroleum ether 1:1 containing 1% glacial acetic acid).

$^1$H-NMR (400 MHz, CDCl$_3$): δ=1.77, 1.97 (2×s, 6H), 1.80 (d, 3H, J=6.8 Hz), 4.03, 4.20 (2×d, 2H, J=13.5 Hz), 4.74 (bs, 1H, OH), 4.92 (q, 1H, J=6.4 Hz) ppm. C$_8$H$_{13}$BrO$_5$S (301.15, 299.97), ESI-MS: (M−H) 299.03.

A7)

(2-Oxo-propylsulfanyl)-essigsäureethylester

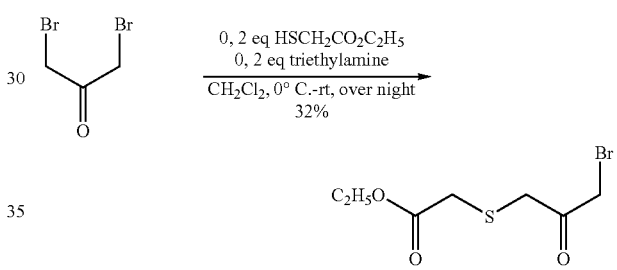

In analogy to procedure A2, an access of 1,3-dibromoacetone (lachrymatory) is used as bromide. The resulting compound is sensitive to hydrolysis and must be stored under anhydrous conditions and at low temperature.

C$_7$H$_{11}$BrO$_3$S (254)—found: 255 (M+H)

Building Block B (Northern Half)

B1)

tert-Butyl 2-acetoxyacetoacetate

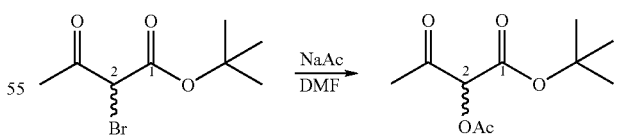

To a suspension of sodium acetate (30.76 g, 375 mmol) in DMF (250 mL) was added dropwise tert-Butyl 2-bromoacetoacetate (59.27 g, 250 mmol). After stirring at ambient temperature for 90 minutes, water (415 mL) was added, followed by extraction with ethyl acetate (3×325 mL). The combined organic layers were washed with water (3×325 mL) and brine (325 mL), dried over Na$_2$SO$_4$ and after filtration, the solvent was removed in vacuo. The resulting oil was purified by distillation (12 mbar, 128°)

¹H-NMR (200 MHz, CDCl₃): δ=1.50 (s, 9H, C(C$\underline{H}_3$)₃), 2.22 (s, 3H, C$\underline{H}_3$COO), 2.34 (s, 3H, C$\underline{H}_3$CO), 5.41 (s, 1H, CH) ppm $C_{10}H_{16}O_5$ (216.23, 216.10), MS (CI): m/z (%)=117 (19), 143 (12), 161 (100), 205 (43), 207 (12), 217 (18); HRMS: calcd (MH⁺) 217.1076, found 217.1046.

B2)

Z-2-Acetoxy-2-acetyl-5,9-dimethyl-deca-4,8-dienoic acid, tert-butyl ester

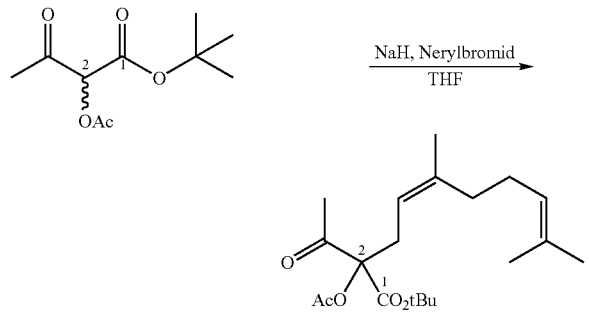

tert-butyl 2-acetoxyacetoacetate (B1) (19.5 g, 90 mmol) was added dropwise to a stirred suspension of NaH (2.59 g, 108 mmol) in THF (180 mL) at 0° C. After the liberation of hydrogen gas stopped, nerylbromide (19.6 g, 90 mmol) was added dropwise at 0° C. Afterwards the ice bath was removed and the mixture stirred at room temperature for 16 hours. The resulting mixture was diluted with ether (750 mL), washed with water (3 200 mL) and brine (1 200 mL), dried over Na₂SO₄, filtered and concentrated in vacuo. The crude product was used without further purification.

¹H-NMR (400 MHz, CDCl₃): δ=1.46 (s, 9H, C(C$\underline{H}_3$)₃), 1.60 (s, 3H, =C(C$\underline{H}_3$)), 1.68 (s, 3H, =C(C$\underline{H}_3$)), 1.70 (s, 3H, =C(C$\underline{H}_3$)), 2.00-2.05 (m, 4H, CH₂-6, CH₂-7), 2.16 (s, 3H, C$\underline{H}_3$COO), 2.31 (s, 3H, C$\underline{H}_3$CO), 2.82-2.87 (m, 2H, CH₂-3), 5.00-5.09 (m, 2H, CH-4, CH-8) ppm. MS (CI): m/z (%)=353 (13) (MH⁺), 298 (21), 297 (100), 279 (14), 255 (10), 253 (13), 237 (27), 219 (20), 209 (65), 193 (10), 175 (6), 153 (7), 137 (16); HRMS: calcd (MH⁺) 353.2328, found 353.2324.

B3)

(4Z,8E)-2-Acetoxy-2-acetyl-5,9-dimehtyl-10-hydroxy-deca-4,8-dienoic acid tert-butylester

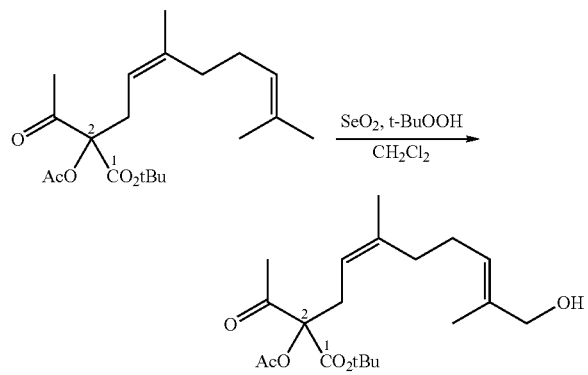

Powdered seleniumdioxide (0.16 g, 1.42 mmol) was suspended in CH₂Cl₂ (50 mL), a 70% tert-butylhydroperoxide solution (10.2 g, 79.5 mmol) was added and the resulting mixture was stirred at room temperature for 30 minutes. Then B2 (10.0 g, 28.4 mmol) was added and stirring continued for 48 hours. After concentrating in vacuo, toluene (50 mL) was added and subsequently removed in vacuo (removal of excess tert-butylhydroperoxide). The procedure was repeated three times and the obtained slightly yellow oil was separated by flash chromatography (ethyl acetate-petroleum ether 1:2)

¹H-NMR (250 MHz, CDCl₃): δ=1.45 (s, 9H, C(C$\underline{H}_3$)₃), 1.66 (s, 3H, =C(C$\underline{H}_3$)), 1.71 (s, 3H, =C(C$\underline{H}_3$)), 1.90-2.15 (m, 4H, CH₂-6, CH₂-7), 2.15 (s, 3H, C$\underline{H}_3$COO), 2.31 (s, 3H, C$\underline{H}_3$CO), 2.85-2.88 (m, 2H, CH₂-3), 3.99 (s, 2H, CH₂-10), 5.02 (m, 1H, CH-4), 5.38 (m, 1H, CH-8) ppm. $C_{20}H_{32}O_6$ (368.46, 368.22), MS (CI): m/z (%)=369 (6) [M+H]⁺, 329 (6), 311 (26), 295 (100), 271 (11), 253 (24), 235 (14), 203 (10), 169 (9), 135 (10); HRMS: calcd (MH⁺) 369.2277, found 369.2288.

B4)

Z-(9S)-2-Acetoxy-2-acetyl-5,9-dimethyl-10-hydroxy-deca-4-enoic acid, tert-butylester

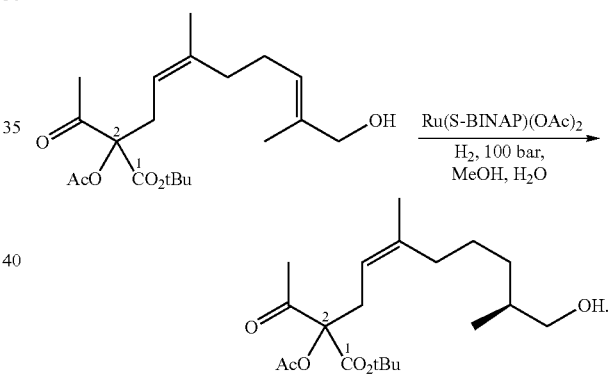

B3 (7.94 g, 21.6 mmol) was dissolved in a mixture of absolute methanol (15.0 mL) and water (750 µl). The solution was degassed with three freeze-thaw-cycles before Ru(S-BINAP)(OAc)₂ (185 mg, 1 mol %) was added and put in an autoclave under nitrogen atmosphere together with a magnetic stirring bar. After threefold purging with hydrogen (5.0 quality) the autoclave was set under a pressure of 100 bar hydrogen (5.0 quality) and stirred at room temperature for 22 h. The hydrogen pressure was released and the solution concentrated in vacuo. The obtained brown oil was purified by flash chromatography (ethyl acetate-petroleum ether 1:2).

¹H-NMR (250 MHz, CDCl₃): δ=0.91 (d, 3H, J=6.4 Hz, 9-CH₃), 1.45 (s, 9H, C(C$\underline{H}_3$)₃), 1.68 (s, 3H, 5-CH₃), 1.0-2.06 (m, 7H, CH₂-6,7,8, CH-9), 2.15 (s, 3H, C$\underline{H}_3$COO), 2.31 (s, 3H, C$\underline{H}_3$CO), 2.84-2.88 (m, 2H, CH₂-3), 3.41 (dd, AB, J₁=10.5 Hz, J₂=6.3 Hz, 1H, CH₂-10), 3.49 (dd, AB, J₁=10.5 Hz, J₂=5.9 Hz, 1H, CH₂-10), 5.00 (t, 1H, CH-4) ppm. $C_{20}H_{34}O_6$ (370.48, 370.24), MS (CI): m/z (%)=369 (6) [M+H]⁺; HRMS: calcd (MH⁺) 371.2433, found 371.2420

B5)

Z-(10S)-3-Acetoxy-11-hydroxy-6,10-dimethyl-5-indecent-2-one

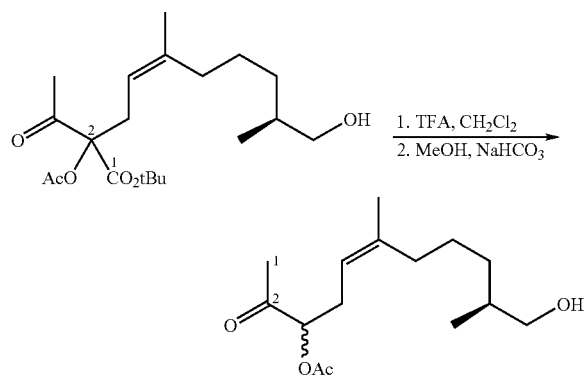

B4 (1.03 g, 2.79 mmol) was dissolved in CH$_2$Cl$_2$ (28 mL) and TFA (2.80 mL) was added. After stirring for two hours at room temperature, all volatile matter was removed in vacuo and the remaining oil was dissolved in methanol (28 mL). NaHCO$_3$ (5.6 mL) was added and the suspension was stirred for 140 minutes at ambient temperature before dilution with ether (200 mL). The organic layer was washed with water (2×50 mL), brine (50 mL) and dried over Na$_2$SO$_4$. Filtration and removal of the solvents in vacuo gave a slightly yellow oil which was purified by flash chromatography (ethyl acetate-petroleum ether 2:3).

$^1$H-NMR (400 MHz, CDCl$_3$): δ=0.92 (d, 3H, J=6.6 Hz, 10-CH$_3$), 1.00-1.20 (m, 1H), 1.30-1.50 (m, 3H), 1.60 (m, 1H), 1.70 (s, 3H, CH$_3$-6), 2.01 (m, 2H), 2.14, 2.16 (2×s, 6H, CH$_3$-1, CH$_3$COO) 2.48 (m, 2H, CH$_2$-4), 3.46 (m, 2H, CH$_2$-1), 4.98 (m, 1H, CH$_3$-3), 5.11 (m, 1H, CH$_3$-5) ppm. C$_{15}$H$_{26}$O$_4$ (270.36, 270.18), MS (ESI-MS): m/z (%)=563.3 (100) [2M+Na]$^+$, 293.0 (54) [M+Na]$^+$, 271.1 (7) [M+H]$^+$

B6)

Z-(10S)-3-Acetoxy-11-tert-butyldimethylsilyloxy-6,10-dimethyl-5-undecen-2-one

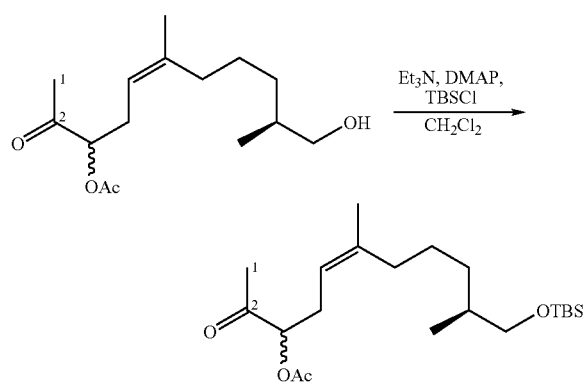

B5 (528 mg, 1.95 mmol) was dissolved in absolute CH$_2$Cl$_2$ (10.0 mL). After addition of triethylamine (541 μl, 3.90 mmol) and DMAP (12 mg, 0.10 mmol), the mixture was cooled to 0° C. After stirring for five minutes at this temperature, TBDMSCI (368 mg, 2.44 mmol) was added and the solution was stirred over night at rt. Methanol (460 μl) was added and after stirring for 30 min all solvents were removed in vacuo. Ether (15 mL) as well as sat. NH$_4$Cl (15 mL) were added and after intensive stirring and separation, the aqueous phase was extracted with ether (2×10 mL). The combined organic layers were washed with brine (15 mL), dried over Na$_2$SO$_4$, filtered and concentrated in vacuo. The obtained oil was purified by flash chromatography (ethyl acetate-petroleum ether 1:10).

$^1$H-NMR (400 MHz, CDCl$_3$): δ=0.02 (s, 6H, Si(CH$_3$)$_2$), 0.83 (d, 3H, J=6.4 Hz, 10-CH$_3$), 0.86 (s, 9H, SiC(CH$_3$)$_3$), 0.94-1.07 (m, 1H), 1.20-1.42 (m, 3H), 1.46-1.58 (m, 1H), 1.66 (s, 3H, 6-CH$_3$), 1.89-2.01 (m, 2H), 2.10, 2.12 (2×s, 6H, CH$_3$-1, CH$_3$COO), 2.38-2.47 (m, 2H, CH$_2$-4), 3.33 (dd, 1H, J=9.8 Hz, J=6.4 Hz, CH$_2$-11), 3.39 (dd, 1H, J=10 Hz, J=6.0 Hz, CH$_2$-11), 4.94 (t, 1H, J=6.4 Hz, CH-3), 5.03-5.07 (m, 1H, CH-5) ppm. C$_{21}$H$_{40}$O$_4$Si (384.63, 384.27), MS (CI): m/z (%)=385 (13) [M+H]$^+$, 327 (13), 267 (26), 253 (6), 193 (40), 175 (62), 117 (100). HRMS: calcd (MH$^+$) 385.2774, found 385.2785

B7)

Z-(10S)-11-(tert-Butyldimethylsilyloxy)-3-hydroxy-6,10-dimethyl-5-undecen-2-one

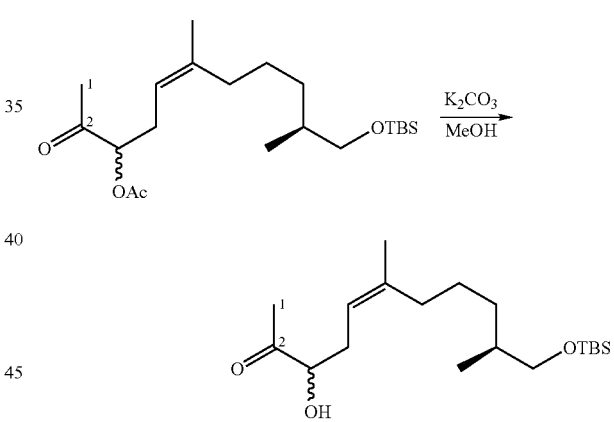

B6 (1.94 g, 5.05 mmol) was dissolved in methanol (20.0 mL) and sat. potassium carbonate solution (400 μl) was added. After stirring at ambient temperature for 14 minutes, brine (30 mL) was added and extraction with diethylether (5×30 mL) followed. The combined organic layers were washed with brine (50 mL) and dried over Na$_2$SO$_4$. After filtration and removal of the solvent in vacuo, the remaining oil was purified via flash chromatography (ethyl acetate-petroleum ether 1:4)

$^1$H-NMR (400 MHz, CDCl$_3$): δ=0.04 (s, 6H, Si(CH$_3$)$_2$), 0.86 (d, 3H, J=6.4 Hz, 10-CH$_3$), 0.89 (s, 9H, SiC(CH$_3$)$_3$), 1.00-1.65 (m, 5H, CH$_2$-8, 9, CH-10), 1.70 (s, 3H, 6-CH$_3$), 1.96-2.04 (m, 2H, CH$_2$-7), 2.19 (s, 3H, CH$_3$-1), 3.44 (m, 2H, CH$_2$-11), 4.19-4.23 (m, 1H, CH-3), 5.08-5.11 (m, 1H, CH-5) ppm. C$_{19}$H$_{38}$O$_3$Si (342.59, 342.26), HRMS: calcd 342.2590, found 342.2583

B8)

(R)-α-Methoxyphenylactic acid, Z-(1S,8S)-1-acetyl-9-(tert-butyldimethylsilyloxy)-4,8-dimethylnon-3-enyl ester

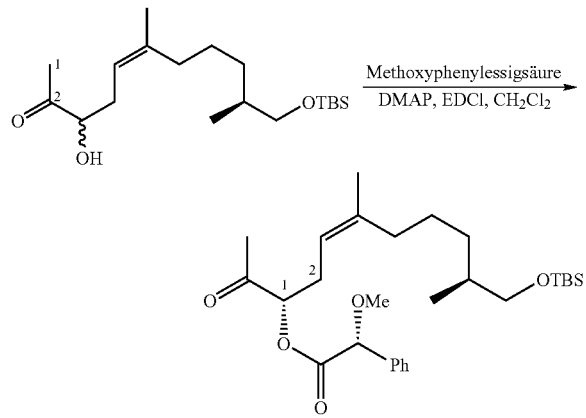

To a solution of B7 (2.41 g, 7.04 mmol), (R)-α-methoxyphenylacetic acid (1.28 g, 7.75 mmol) and DMAP (86 mg, 0.70 mmol) in CH$_2$Cl$_2$ (72.0 mL) was added EDCI (2.70 g, 14.09 mmol), and the solution was stirred 2 hours at ambient temperature. Then diethylether (250 mL) was added and the resulting suspension was extracted with water (233 100 mL) and brine (100 mL). The organic layer was dried over Na$_2$SO$_4$, filtered and concentrated in vacuo. The remaining yellow oil contained two diastereomeric esters, which were separated by flash chromatography (ethyl acetate-petroleum ether 1:10)

$^1$H-NMR (400 MHz, CDCl$_3$): δ=0.01 (s, 6H, Si(CH$_3$)$_2$), 0.83 (d, 3H, J=6.8 Hz, 8-CH$_3$), 0.86 (s, 9H, SiC(CH$_3$)$_3$), 0.92-1.62 (m, 5H, CH$_2$-6, 7, CH-8), 1.63 (s, 3H, 4-CH$_3$), 1.76 (s, 3H, CH$_3$CO), 1.84-2.01 (m, 2H, CH$_2$-5), 2.34-2.50 (m, 2H, CH$_2$-2), 3.35 (dd, 1H, J=9.7 Hz, J=6.4 Hz, CH$_2$-9), 3.39 (dd, 1H, J=9.8 Hz, J=6.1 Hz, CH$_2$-9), 3.42 (s, 3H, OCH$_3$), 4.79 (s, 1H, CHOCH$_3$), 4.93-5.30 (m, 2H, CH-1, 3), 7.35-7.49 (m, 5H, phenyl-CH) ppm. C$_{28}$H$_{46}$O$_5$Si (490.75, 490.31), HRMS: calcd 490.3115, found 490.3107

B9)

(R)-α-Methoxyphenylacetic acid, Z-(1S,8S)-9-(tert-butyldimethylsilyloxy)-4,8-dimethyl-1-[E-1-methyl-2-(2-methylthiazol-4-yl)-vinyl]-non-3-enyl ester

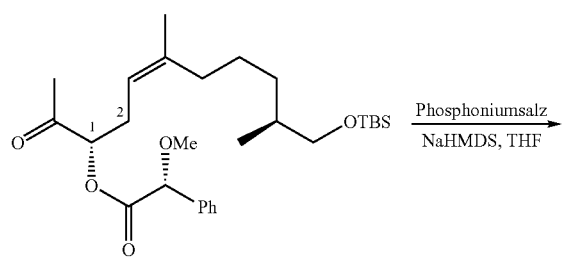

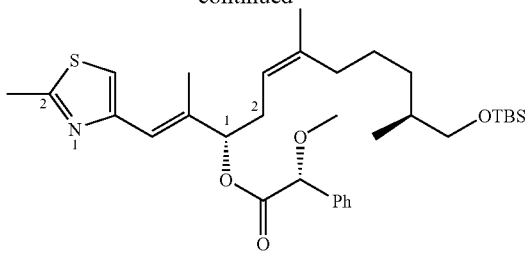

A solution of tributyl-(2-methylthiazol-4-ylmethyl)-phosphonium chloride (1.02 g, 2.92 mmol) in abs. THF (19.0 mL) was cooled to −65° C. and sodium-hexamethyldisilazid (2 M solution in THF, 1.56 mL, 3.12 mmol) was added dropwise. After stirring for 10 min, a solution of B8 (1.19 g, 2.43 mmol) in abs. THF (8.0 mL) was added slowly. After 60 min stirring at −65° C., saturated NH$_4$Cl (45 mL) was added. Extraction with ether (5×25 mL), washing the combined organic layers with water (3 30 mL) and brine (1 50 mL), drying over Na$_2$SO$_4$, filtration and removal of the solvent in vacuo gave the crude product. It was purified by flash chromatography (ethyl acetate-petroleum ether 1:5).

$^1$H-NMR (300 MHz, CDCl$_3$): δ=0.02 (s, 6H, Si(CH$_3$)$_2$), 0.84 (d, 3H, J=6.9 Hz, 8-CH$_3$), 0.89 (s, 9H, SiC(CH$_3$)$_3$), 0.95-2.05 (m, 7H), 1.51 (s, 3H, 4-CH$_3$), 2.05 (s, 3H), 2.29 (t, 2H, J=7.2 Hz, CH$_2$-2), 2.70 (s, 3H, SCCH$_3$), 3.30-3.46 (m, 2H, CH$_2$-9), 3.41 (s, 3H, OCH$_3$), 4.75-4.80 (m, 1H, CH-1), 4.78 (s, 1H, CHOCH$_3$), 5.25 (t, 1H, J=6.6 Hz, CH-3), 6.48 (s, 1H), 6.90 (s, 1H), 7.32-7.37 (m, 3H), 7.43-7.46 (m, 2H) ppm. C$_{33}$H$_{51}$NO$_4$Ssi (585.91, 585.33), HRMS: calcd (MH$^+$) 586.3390, found 586.3381

B10)

(1E,5Z,3S, 10s)-11-(tert-Butyldimethylsilyloxy)-2,6,10-trimethyl-1-(2-methylthiazol-4-yl)-undeca-1,5-dien-3-ol

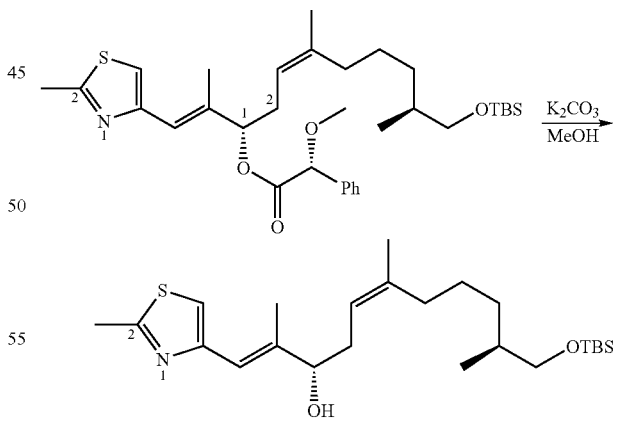

To a solution of B9 (0.59 g, 1.00 mmol) in methanol (10.0 mL) was added K$_2$CO$_3$ (0.28 g, 2.00 mmol) at ambient temperature. After stirring for 90 minutes, the solvents were removed in vacuo and ethyl acetate (40 mL) was added. The organic layer was washed with water (3 10 mL) and brine (10 mL), dried over Na$_2$SO$_4$, filtered and concentrated in vacuo. The remaining slightly yellow oil was purified by flash chromatography (ethyl acetate/petroleum ether 1:3).

¹H-NMR (300 MHz, CDCl₃): δ=0.03 (s, 6H, Si(C$\underline{H}$₃)₂), 0.86 (d, J=6.7 Hz, 3H, 10-CH₃), 0.89 (s, 9H, SiC(C$\underline{H}$₃)₃), 1.00-1.65 (m, 5H), 1.71 (s, 3H, 6-CH₃), 1.84 (d, 1H, OH), 2.01-2.08 (m, 2H), 2.05 (s, 3H, 2-CH₃), 2.35 (m, 2H, CH₂-4), 2.71 (s, 3H, SCC$\underline{H}$₃), 3.35 (dd, J=9.7 Hz, J=6.5 Hz, 1H, CH₂-11), 3.44 (dd, J=9.7 Hz, J=5.9 Hz, l1H, CH₂-11), 4.13 (m, 1H, CH-3), 5.16 (m, 1H, CH-5), 6.56 (s, 1H, CH-1), 6.94 (s, 1H, CHS) ppm. MS (CI): m/z (%)=438 (13) [M+H]⁺, 420 (27), 396 (4), 380 (12), 364 (4), 259 (27), 213 (100). C₂₄H₄₃NO₂SSi (437.75, 437.28), HRMS: calcd (M+Na)⁺ 460.268, found 460.2676.

B11)

(R)-α-Methoxyphenylacetic acid, Z-(1S,8S)-9-(tert-butyldimethylsilyloxy)-4,8-dimethyl-1-[(1E)-1-methyl-2-(2-methylthiazol-4-yl)-vinyl]-non-3-enyl ester

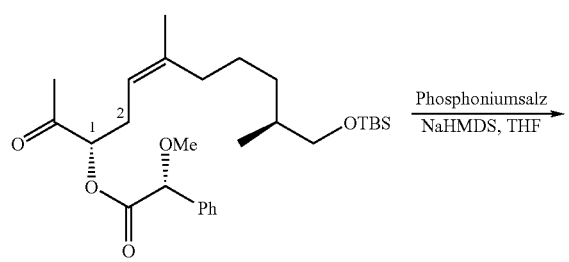

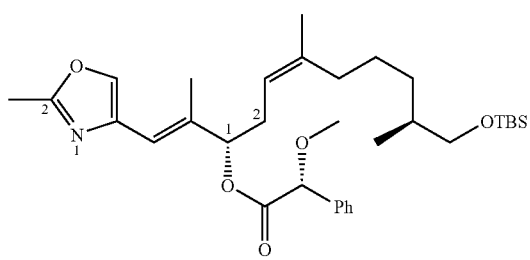

A solution of tributyl-(2-methyloxazol-4-ylmethyl)-phosphonium bromide (0.43 g, 1.12 mmol) in abs. THF (10 mL) is cooled to −78° C., followed by dropwise addition of NaHMDS (2 M in THF, 0.64 mL, 1.12 mmol). After 10 min stirring, a solution of B8 (0.48 g, 0.97 mmol) in abs. THF (4 mL) is added, and all stirred for 120 min at −78° C. The reaction mixture is quenched with NH₄Cl-soln. (10 mL) and extracted with Et₂O (5×20 mL). The combined organic extracts are washed with water (3 15 mL) and brine (1 20 mL), dried over Na₂SO₄, and the solvent removed in vacuo. The crude product is purified by flashchromatography (PE:EA 4:1).

¹H-NMR (300 MHz, CDCl₃): δ=0.03 (s, 6H, Si(C$\underline{H}$₃)₂), 0.83 (d, 3H, 8-CH₃), 0.89 (s, 9H, SiC(C$\underline{H}$₃)₃), 0.93-1.92 (m, 7H), 1.58 (s, 3H, 4-CH₃), 1.91 (s, 3H), 2.25 (t, 2H, CH₂-2), 2.45 (s, 3H, NCC$\underline{H}$₃), 3.32-3.39 (m, 2H, CH₂-9), 3.41 (s, 3H, OCH₃), 4.72 (t, 1H, CH-1), 4.77 (s, 1H), 5.23 (t, 1H, CH-3), 6.23 (s, 1H), 7.26-7.46 (m, 5H), 7.44 (s, 1H) ppm.

B12)

(1E,5Z,3S,10S)-11-(tert-Butyldimethylsilyloxy)-2,6,10-trimethyl-1-(2-methyloxazol-4-yl)-undeca-1,5-dien-3-ol

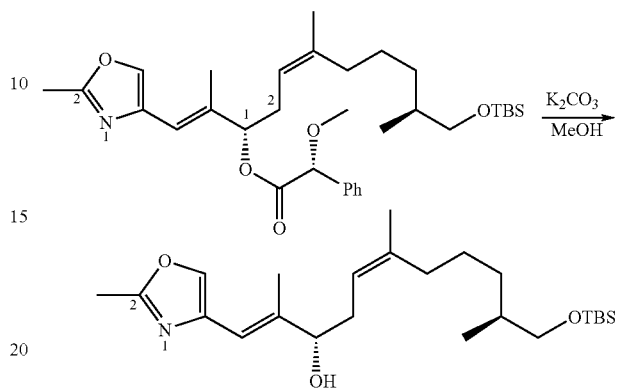

To a solution of B11 (0.2 g, 0.35 mmol) in methanol (10.0 mL) was added K₂CO₃ (95 mg) and stirred at room temperature for 2.5 h. The solvent is removed in vacuo and ethyl acetate (40 mL) is added. The organic layer is washed with water (3 10 mL) and brine (10 mL), dried over Na₂SO₄, filtered and concentrated in vacuo. The crude product was purified by flash chromatography (ethyl acetate/petroleum ether 1:3).

¹H-NMR (300 MHz, CDCl₃): δ=0.01 (s, 6H, Si(C$\underline{H}$₃)₂), 0.84 (d, 3H, 10-CH₃), 0.86 (s, 9H, SiC(C$\underline{H}$₃)₃), 1.29-1.70 (m, 5H), 1.67 (s, 3H, 6-CH₃), 1.89 (s, 3H, 2-CH₃), 1.97-2.01 (m, 2H, CH₂-7), 2.27-2.31 (m, 2H, CH₂-4), 2.42 (s, 3H, NCC$\underline{H}$₃), 3.32 (dd, 1H, CH₂-11), 3.40 (dd, 1H, CH₂-11), 4.05-4.13 (m, 1H, CH-3), 5.10 (t, 1H, CH-5), 6.26 (s, 1H, CH-1), 7.44 (s, 1H, OC$\underline{H}$) ppm. C₂₄H₄₃NO₃Si (421.69, 421.30), HRMS: calcd (M+Na)⁺ 444.2904, found 444.2904

B13)

(R)-α-Methoxyphenylacetic acid, (3Z,8E,1S)-9-(tert-butyldimethylsilyloxy)-4,8-dimethyl-1-[(1E)-1-methyl-2-(6-methyl-pyridin-2-yl)-vinyl]-non-3,7-dienyl ester

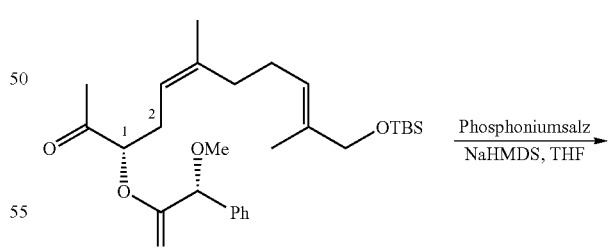

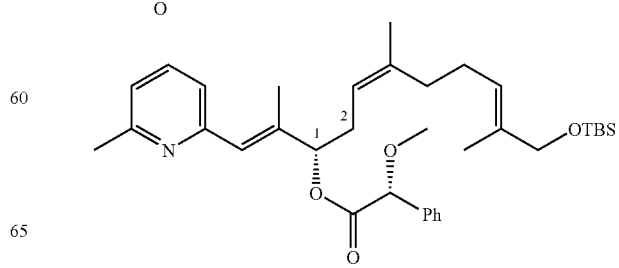

A solution of tributyl-(6-methylpyridin-2-ylmethyl)-phosphonium chloride (1.3 g, 3.78 mmol) in abs. THF (20 mL) is cooled to −78° C. and NaHMDS (2 M in THF, 0.75, 2.04 ml, 4.1 mmol) is added dropwise. After 10 min stirring, a solution of B8 B8 (1.59 g, 3.15 mmol) in abs. THF (4 mL) is added, and all stirred for 3 h at −78° C. The reaction mixture is quenched with NH$_4$Cl-soln. (50 mL) and extracted with Et$_2$O (5×30 mL). The combined organic extracts are washed with water (3 20 mL) and brine (1 50 mL), dried over Na$_2$SO$_4$, and the solvent removed in vacuo. The crude product is purified by flashchromatography (PE: EA 8:1).

$^1$H-NMR (300 MHz, CDCl$_3$): δ=0.03 (s, 6H, Si(CH$_3$)$_2$), 0.83 (d, 3H, 8-CH$_3$), 0.89 (s, 9H, SiC(CH$_3$)$_3$), 0.93-1.92 (m, 7H), 1.58 (s, 3H, 4-CH$_3$), 1.91 (s, 3H), 2.25 (t, 2H, CH$_2$-2), 2.45 (s, 3H, NCCH$_3$), 3.32-3.39 (m, 2H, CH$_2$-9), 3.41 (s, 3H, OCH$_3$), 4.72 (t, 1H, CH-1), 4.77 (s, 1H), 5.23 (t, 1H, CH-3), 6.23 (s, 1H), 6.93 (d, 1H, CH$_{Pyr}$), 7.06 (d, 1H, CH$_{Pyr}$), 7.22-7.58 (m, 6H), ppm.

B14)

(1E,5Z,9E,3S)-11-(tert-Butyldimethylsilyloxy)-2,6,10-trimethyl-1-(6-methyl-pyridin-2-yl-)-undeca-1,5,9-trien-3-ol

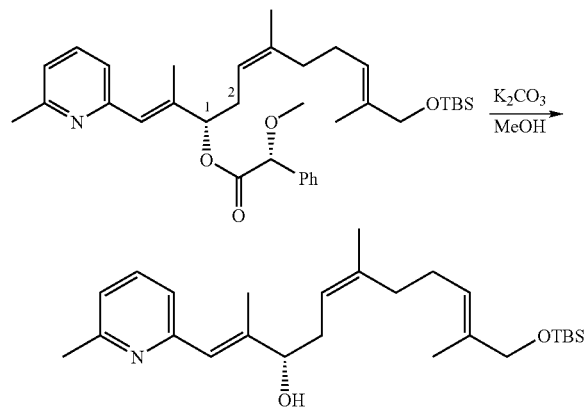

To a solution of B13 (0.55 g, 0.96 mmol) in methanol (12.0 mL) was added K$_2$CO$_3$ (260 mg, 1.91 mmol) and stirred at room temperature for 2.5 h. The solvent is removed in vacuo and ethyl acetate (40 mL) is added. The organic layer is washed with water (3 10 mL) and brine (10 mL), dried over Na$_2$SO$_4$, filtered and concentrated in vacuo. The crude product was purified by flash chromatography (ethyl acetate/petroleum ether 1: 2.5).

$^1$H-NMR (300 MHz, CDCl$_3$): δ=0.06 (s, 6H, Si(CH$_3$)$_2$), 0.90 (s, 9H, SiC(CH$_3$)$_3$), 1.46-2.18 (m, 4H), 1.61 (s, 3H, 10-CH$_3$), 1.75 (s, 3H, 6-CH$_3$ ), 2.05 (s, 3H, 2-CH$_3$), 2.36-2.40 (m, 2H, CH$_2$-4), 2.56 (s, 3H, NCCH$_3$), 4.01 (s, 2H, CH$_2$-11), 4.17 (t, 1H, CH-3), 5.22 (t, 1H, CH-5), 5.40 (t, 1H, CH-9), 6.59 (s, 1H, CH-1), 6.97 (d, 1H, CH-5$_{Pyr}$), 7.07 (d, 1H, CH-3$_{Pyr}$), 7.54 (d, 1H, CH-4$_{Pyr}$) C$_{26}$H$_{43}$NO$_2$Si (429.31, 429.71), HRMS: calcd (M+H)$^+$ 430.3163 found 430.3130

C (Combinatorial Connection and Cyclization of Building Blocks A and B)

C1)

(1S,3Z,8S)-9-{[tert-butyl(dimethyl)silyl]oxy}-4,8-dimethyl-1-[(E)-1-methyl-2-(2-methyl-1,3-thiazol-4-yl)vinyl]non-3-en-1-yl[(3-bromo-1,1-dimethyl-2-oxobutyl)thio]acetate

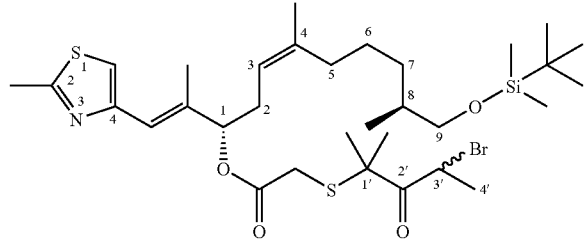

(3-Bromo-1,1-dimethyl-2-oxo-butylsulfanyl)-acetic acid (A5, 0.10 g, 0.37 mmol), (1E,5Z,3S,10S)-11-(tert-Butyldimethylsilyloxy)-2,6,10-trimethyl-1-(2-methylthiazol-4-yl)-undeca-1,5-dien-3-ol (B10, 0.11 g, 0.25 mmol) and DMAP (6 mg, 0.049 mmol) were dissolved in CH$_2$Cl$_2$ (4 mL) and cooled to 0° C. EDCI (0.06 g, 0.32 mmol) was added and after stirring for 10 minutes, the mixture was allowed to come to room temperature and stirring was continued for 18 hours. After addition of Et$_2$O (100 mL), the organic layer was washed with halfconcentrated NaCl-solution (40 mL) and brine (40 mL). The organic layer was dried over Na$_2$SO$_4$, filtered and concentrated in vacuo. The remaining oil was purified by flash chromatography (ethyl acetate-petroleum ether 1:5).

$^1$H-NMR (400 MHz, CDCl$_3$): δ=−0.08 (s, 6H, Si(CH$_3$)$_2$), 0.83 (d, J=6.4 Hz, 3H), 0.86 (s, 9H, SiC(CH$_3$)$_3$), 0.94-1.58 (m, 5H), 1.44 (s, 3H, C(CH$_3$)$_2$), 1.60 (s, 3H, C(CH$_3$)$_2$), 1.63 (s, 3H), 1.73, 1.74* (2×d, 3H, J=5.2 Hz, CHBrCH$_3$), 1.96 (t, 2H), 2.03 (s, 3H), 2.29-2.47 (m, 2H), 2.67 (s, 3H, SCCH$_3$), 2.99 (d, 1H, J=15.4 Hz, SCH$_2$), 3.11, 3.12* (2×d, 1H, J=15.4 Hz, SCH$_3$), 3.32 (d, 1H, J=6.6 Hz, J=9.7 Hz CH$_2$O), 3.40 (d, 1H, J=6.6 Hz, J=9.7 Hz CH$_2$O), 5.00 (t, 1H), 5.06 (2×q, 1H, CHBr), 5.13-5.24 (m, 1H, OCH), 6.46 (s, 1H), 6.92, 6.93* (2×s, 1 H, CHS) ppm. *second diastereomer C$_{32}$H$_{54}$BrNO$_4$S$_2$Si (688.89, 687.24), MS (CI): m/z (%)=802 (0.9) [M+H]$^+$, 800 (0.6) [M+H]$^+$ , 420 (75), 168 (100). HRMS: calcd (M+Na)$^+$ 824.3557, found 824.3568.

C2)

(1S,3Z,8S)-9-hydroxy-4,8-dimethyl-1-[(E)-1-methyl-2-(2-methyl-1,3-thiazol-4-yl)vinyl] non-3-en-1-yl [(3-bromo-1,1-dimethyl-2-oxobutyl)thio]acetate

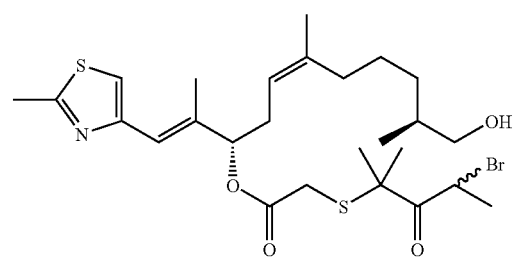

(137 mg, 0.19 mmol) was dissolved in a 1:1-mixture of CH$_2$Cl$_2$ and MeOH (5 mL) and cooled to 0° C. After addition of CSA (46 mg, 0.19 mmol), the solution was stirred for 2.5 hours at 0° C. After addition of triethylamine (42 µl, 0.29 mmol), the solvents were removed in vacuo and the remaining oil was purified by flash chromatography (ethyl acetate-petroleum ether 1:2).

$^1$H-NMR (400 MHz, CDCl$_3$): δ=0.90 (d, J=6.4 Hz, 3H, CHCH$_3$), 0.83-1.61 (m, 5H), 1.46 (s, 3H, C(CH$_3$)$_2$), 1.62 (s, 3H, C(CH$_3$)$_2$), 1.66 (s, 3H), 1.76* (2×d, 3H, J=6.0 Hz, CHBrCH$_3$), 2.00 (t, 2H, J=6.0 Hz), 2.05 (s, 3H), 2.09-2.24 (bs, 1H, OH), 2.30-2.54 (m, 2H), 2.69 (s, 3H, SCCH$_3$), 3.02 (d, 1H, J=14.8 Hz, SCH$_2$), 3.12, 3.16* (2×d, 1H, J=6.0 Hz, SCH$_2$), 3.41 (d, 1H, J=6.2 Hz, J=10.6 Hz CH$_2$O), 3.47 (d, 1H, J=6.2 Hz, J=10.6 Hz CH$_2$O), 5.04 (t, 1H), 5.08* (2×q, 1H, CHBr), 5.17-5.25 (m, 1H, OCH), 6.46 (s, 1H), 6.92, 6.93* (2×s, 1H, CHS) ppm. (*second diastereomer) HRMS: calcd (M+Na) 596.1478, found 596.1474

C3)

(1S,3Z,8S)-4,8-dimethyl-1-[(E)-1-methyl-2-(2-methyl-1,3-thiazol-4-yl)vinyl]-9-oxonon-3-en-3-en-1-yl [(3-bromo-1,1-dimethyl-2-oxobutyl)thio]acetate

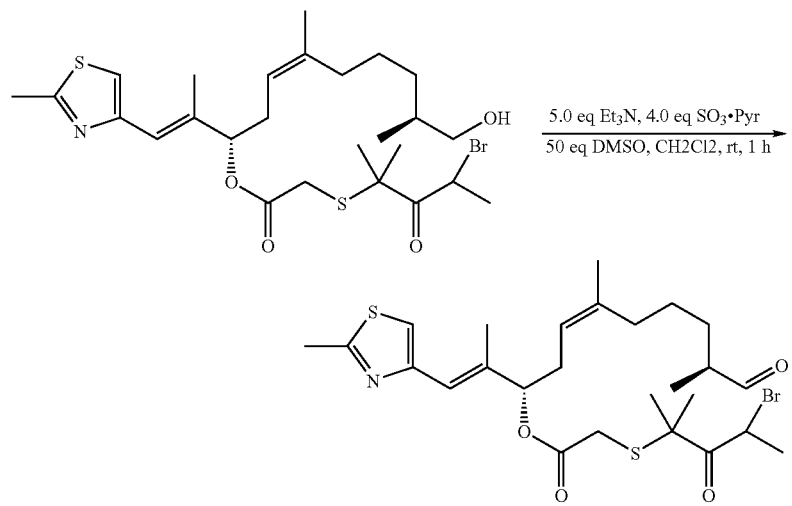

C2 (97 mg, 0.17 mmol) was dissolved in a mixture of CH$_2$Cl$_2$ (5 mL), DMSO (0.6 mL) and triethylamine (85 mg, 0.84 mmol). After cooling to 0° C. a SO$_3$*Pyridine complex (107 mg) was added and the resulting mixture was stirred 20 min at 0° C. Dilution with diethylether (100 mL) was followed by washing with water (2×20 mL) and brine (2×20 mL) drying over Na$_2$SO$_4$, filtration and concentration in vacuo gave the crude product, that can be purified by flash chromnatography (PE:EA=4:1).

$^1$H-NMR (400 MHz, CDCl): δ=1.02 (d, 3H), 1.20-1.65 (m, 7H), 1.40 (s, 3H, CH$_3$), 1.56 (s, 3H, CH$_3$), 1.59 (s, 3H, CH$_3$), 1.93-1.98 (m, 2H), 2.00 (s, 3H, CH$_3$), 2.22-2.46 (m, 2H), 2.63 (s, 3H, SCCH$_3$), 2.94-3.11 (m, 2H, SCH$_2$), 4.99-5.03 (m, 2H), 5.13-5.17 (m, 1H), 6.42 (s, 1H), 6.90 (s, 1H, CHS), 9.54 (s, 1H) ppm. HRMS: calcd (M+Na) 594.1318, found 594.1329

C4)

(7R,8S,9S,13Z,16S)-8-hydroxy-5,5,7,9,13-pentamethyl-16-[(E)-1-methyl-2-(2-methyl-1,3-thiazol-4-yl)vinyl]-1-oxa-4-thiacyclohexadec-13-ene-2,6-dione (4)

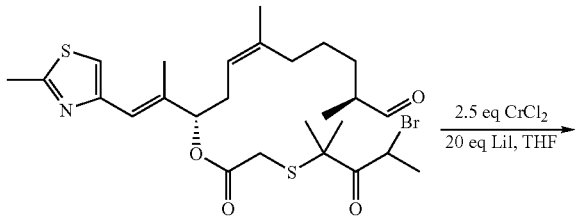

-continued

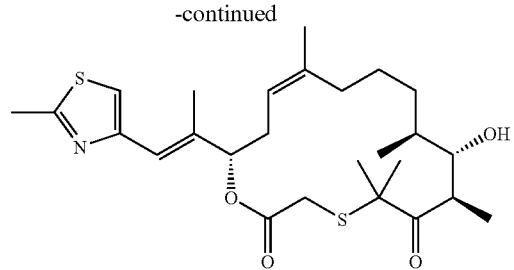

To a suspension of CrCl$_2$ (52 mg, 0.42 mmol) and LiI (45 mg, 0.134 mmol) in dry THF (15 mL) was added a solution of C3 (97 mg, 0.17 mmol) in THF (510 mL) within 80 min via syringe pump. After the addition was finished, the resulting suspension was stirred a further 30 min. at ambient temperature. After quenching with halfconcentrated NH$_4$Cl (10 mL), the organic phase was extracted with ether (3×20 mL). The organic layers were combined and washed twice with demi water (20 mL) as well as with brine (20 mL), dried over $Na_2SO_4$, filtered and concentrated in vacuo. The remaining oil was purified by flash chromatography (ethyl acetate-petroleum ether 1:2).

$^1$H-NMR (500 MHz, $CDCl_3$): δ=1.01 (d, 3H, 9-$CH_3$), 1.17 (d, 3H, 7-$CH_3$), 1.25-1.81 (m, 7H), 1.42, 1.69 (2×s, 6H, 5-$(CH_3)_2$), 2.11 (s, 3H, 1'-$CH_3$), 2.04-2.19 (m, 2H, 15-$CH_2$), 2.31-2.37 (m, 1H, CH-9), 2.70 (s, 3H, $NCCH_3CH$-7), 3.77-3.79 (m, 1H, CH-8), 5.12 (dd, 1H, CH-14), 5.18 (dd, 1H, CH-16), 6.54 (s, 1H), 7.26 (s, 1H, C$\underline{H}$S) ppm. $C_{26}H_{39}NO_4S_2$ (493.72, 493.23), HRMS: calcd $(M+Na)^+$ 516.2212, found 516.2212

C5)

(7R,8R,9S,13Z)-8-Hydroxy-5,5,7,9,13-pentamethyl-16-[(IE)-1-methyl-2-(2-methyl-thiazol-4-yl)-vinyl]-4,4-dioxo-1-oxa-4-thia-cyclohexadec-13-en-2,6-dion

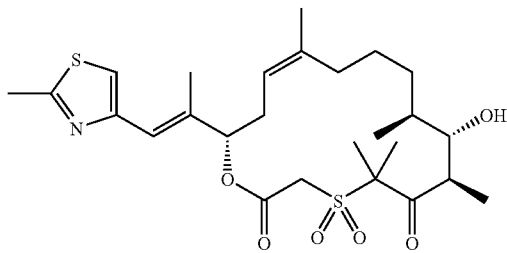

C5 was obtained along the same route as C4 (Steps C1-C3 and Macrocyclization C4) but starting with A6.

$^1$H-NMR (500 MHz, $CDCl_3$): δ=0.99 (d, 3H, 9-$CH_3$), 1.21 (d, 3H, 7-$CH_3$), 1.27-1.88 (m, 7H), 1.57, 1.59 (2×s, 6H, 5-$(CH_3)_2$), 1.83 (s, 3H, 13-$CH_3$), 2.10-2.41 (m, 3H, $CH_2$-15, CH-9), 2.13 (s, 3H, 1'-$CH_3$), 2.77 (s, 3H, NCC$\underline{H}_3$), 3.56-3.58 (m, 1H, CH-7), 3.73-3.76 (m, 1H, CH-8), 3.88-3.98 (2×d, 2H, $CH_2$-3), 5.00-5.06 (m, l1H, CH-14), 5.12-5.18 (m, 1H, CH-16), 6.62 (s, 1H), 7.02-7.05 (s, 1H, C$\underline{H}$S) ppm. $C_{26}H_{39}NO_6S_2$ (525.72, 525.22), HRMS: calcd $(M+Na)^+$ 548.2108, found 548.2108

C6)

(7R,8R,9E,13Z)-8-Hydroxy-5,5,7,9,13-pentamethyl-16-[(1E)-1-methyl-2-(6-methyl-pyridin-2-yl)-vinyl]-1-oxa-4-thia-cyclohexadec-9,13-dien-2,6-dion (Epo D5 type)

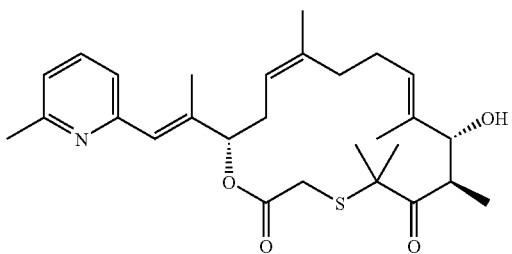

C6 was obtained along the same route as C4 (Steps C1-C3 and Macrocyclization C4) but starting with B 14.

$C_{28}H_{39}NO_4S$ (485.68, 485.26), HRMS: calcd $(M+H)^+$ 486.2671, found 486.26668

C7)

Oxidation of 3-thia-epothilone D (3-Thiaepothilone B oxide mix, containing e.g. 3-thiaepothilone B, -sulfoxide, and -sulfone)

0.5 mg 3-thiaepothilone D was treated with an access of dimethyldioxirane-solution (ca. 1% in acetone) until all educt was consumed. After MS-recording the solvent was removed in vacuo.

Monooxide of 3-thiaepothilone D: $C_{26}H_{39}NO_5S_2$ (509.7), MS: calcd $(M+H)^+$ m/z=510, found 510

D)

Biological Data (Examples)

Proliferation assay GI50: acidic phosphatase, incubation period 5 days, IC-50 (μM)

(Anal. Biochem. 241 (1996) 103)

| Derivative | Batch/Comment | MCF7 breast cancer | L 929 mouse fibroblasts | A 549 lung cancer |
|---|---|---|---|---|
| MC54690 (C4) | 3-thia-epothilone D | 0.045 | 0.274 | 0.009 |
| MC54774 (C7) | 3-Thia-epo D (oxidized) | 0.073 | 0.051 | 0.008 |
| MC54849 | D5-Type . . . | 0.531* | — | — |
| MC54847 | . . . 6,7-Diastereomer | >10* | — | — |
| MC54848 | . . . 6,7-Diastereomer | >10* | — | — |
| MC-C5 | 3-sulfone-Epo D | >10 | | |
| Taxol | reference | 0.003 | 0.270 | 0.006 |

*Incubation 4 days.

We claim:
1. A compound of the general formula (I):

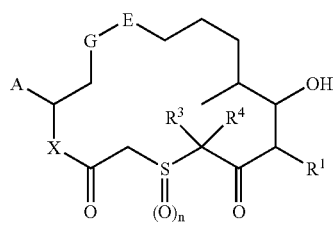

(I)

wherein
A is a heteroalkyl-, heterocycloalkyl-, heteroalkyl-cycloalkyl-, heteroaryl- or heteroarylalkyl group,
G-E is selected from the following groups,

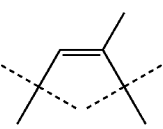 

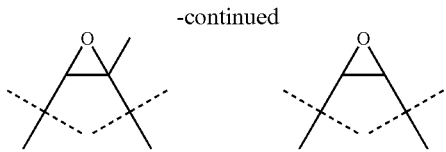

or is part of an optionally substituted cyclopropyl ring, n is 0, 1 or 2, $R^1$ is a $C_1$-$C_4$ alkyl- or a $C_3$-$C_4$-cycloalkyl group, X is oxygen or a group of the formula $NR^2$, wherein $R^2$ is hydrogen, OH, $NH_2$, NH(Alkyl), N(alkyl)$_2$, a alkyl-, alkenyl-, alkynyl-, hetero-alkyl-, aryl-, heteroaryl-, cycloalkyl-, alkylcyclo-alkyl-, heteroalkylcycloalkyl-, heterocycloalkyl-, aralkyl- or a heteroaralkyl group, $R^3$ and $R^4$ are independently of each other hydrogen, a $C_1$-$C_4$ alkyl group or together are part of a cycloalkyl group with 3 or 4 ring atoms, or a pharmacologically acceptable salt, or a pharmacologically acceptable formulation thereof.

2. A compound according to claim 1, wherein A is a group of the formula —C(CH$_3$)=CHR$^5$, —C(C$_2$H$_5$)=CHR$^5$, —C(Cl)=CHR$^5$ or —CH=CHR$^5$, wherein R$^5$ is a heteroaryl- or a heteroarylalkyl group.

3. A compound according to claim 1, wherein A is a group of the general formula (II), (III), (IV), or (V):

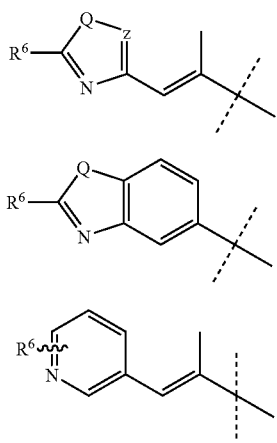

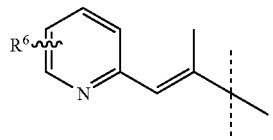

wherein

Q is sulphur, oxygen or a group of the formula NR$^7$, wherein R$^7$ is hydrogen, a C$_1$-C4 alkyl group or a C$_1$-C$_4$-heteroalkyl group, z is nitrogen or a CH group and R$^6$ is a group of the formula OR$^8$ or NHR$^8$, a alkyl-, alkenyl, alkinyl- or a heteroalkyl group, wherein R$^8$ is hydrogen, a C$_1$-C$_4$-alkyl group or a C$_1$-C$_4$-heteroalkyl group.

4. A compound according to claim 3, wherein z is a CH-group.

5. A compound according to claim 3, wherein Q is sulphur or oxygen.

6. A compound according to claim 3, wherein R$^6$ is a group of the formula CH$_3$, CH$_2$OH or CH$_2$NH$_2$.

7. A compound according to claim 1 wherein X is oxygen.

8. A compound according to claim 1, wherein R$^1$ is a methyl group.

9. A compound according to claim 1, wherein R$^3$ and R$^4$ are methyl groups.

10. A method of synthesizing the compound of claim 1 comprising (a) coupling (i) (1,1-Dialkyl-2-oxo-butylsulfanyl)-acetic acid or a derivative thereof selected from the group consisting of sulfoxides, sulfones, esters, amides, 3-haloderivates, (3-bromo-1,1-dimethyl-2-oxo-butylsulfanyl)-acetic acid esters of methanol and ethanol, and sulfoxides of methanol and ethanol to (ii) a compound selected from the group consisting of (1E,5Z,3S,10S)-11-(tert-butyl-dimethylsilyloxy)-2,6,10-trimethyl-1-(2-methyl-thiazol-4-yl)-undeca-1,5-dien-3-ol, (1E,5Z,3S,10S)-11-(tert-butyl-dimethyl-silyloxy)-2,6,10-trimethyl-1-(2-methyloxazol-4-yl)-undeca-1,5-dien-3-ol, and (1E,5Z,3S,10S)-11-(tert-butyl-dimethyl-silyloxy)-2,6,10-trimethyl-1-(2-methyl-pyridine-2-yl)-undeca-1,5,9-trien-3-ol via an esterification reaction, and (b) subjecting the product of step (a) to an aldol condensation reaction, to synthesize the compound of claim 1.

11. A pharmaceutical composition containing a compound according to claim 1 and optionally a carrier and/or adjuvants.

* * * * *